(12) United States Patent
Hoover et al.

(10) Patent No.: US 9,844,930 B2
(45) Date of Patent: Dec. 19, 2017

(54) 3D PRINTING OF DIGESTIBLE SHELLS FOR MEDICAMENTS

(71) Applicant: Xerox Corporation, Norwalk, CT (US)

(72) Inventors: Linn C. Hoover, Webster, NY (US); William J. Hannaway, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 528 days.

(21) Appl. No.: 14/533,201

(22) Filed: Nov. 5, 2014

(65) Prior Publication Data
US 2016/0120808 A1 May 5, 2016

(51) Int. Cl.
| | |
|---|---|
| *A61K 9/20* | (2006.01) |
| *B33Y 80/00* | (2015.01) |
| *B33Y 10/00* | (2015.01) |
| *B33Y 50/00* | (2015.01) |
| *B29C 67/00* | (2017.01) |
| *A61K 9/00* | (2006.01) |
| *A61K 9/48* | (2006.01) |
| *A61J 3/07* | (2006.01) |
| *B29C 64/112* | (2017.01) |
| *A61D 7/00* | (2006.01) |

(52) U.S. Cl.
CPC .......... *B33Y 80/00* (2014.12); *A61J 3/07* (2013.01); *A61K 9/0056* (2013.01); *A61K 9/4825* (2013.01); *B29C 64/112* (2017.08); *B29C 67/0059* (2013.01); *B33Y 10/00* (2014.12); *B33Y 50/00* (2014.12); *A61D 7/00* (2013.01)

(58) Field of Classification Search
CPC ....... A61K 9/0056; A61K 9/48–9/4891; B29C 67/0051–67/0081; B33Y 10/00; B33Y 30/00; B33Y 50/00; B33Y 80/00; A23G 1/0056; A23G 1/202; A23G 3/0097; A23G 3/0242; A23G 3/007–3/0074; A23P 2020/253; A01K 13/003; A01K 15/026; A61D 7/00; A61J 3/07
USPC .......... 53/452–454; 424/439–442; 436/103–104, 138–140; 427/2.14
See application file for complete search history.

(56) References Cited

U.S. PATENT DOCUMENTS

| | | | | |
|---|---|---|---|---|
| 4,857,333 A | * | 8/1989 | Harold | A01K 13/003 424/405 |
| 5,098,715 A | | 3/1992 | McCabe et al. | |
| 5,490,962 A | * | 2/1996 | Cima | A61F 2/022 156/272.8 |
| 6,143,316 A | * | 11/2000 | Hayden | A61K 9/0056 424/438 |
| 6,312,746 B2 | * | 11/2001 | Paluch | A23K 40/20 426/282 |

(Continued)

FOREIGN PATENT DOCUMENTS

WO 2013/112882 A1 8/2013

*Primary Examiner* — Hemant M Desai
*Assistant Examiner* — Valentin Neacsu
(74) *Attorney, Agent, or Firm* — Maginot Moore & Beck LLP (57) ABSTRACT

A method for producing edible medications comprises providing a three-dimensional (3D) model of the edible medication including an internal cavity sized and shaped for receipt of a medicament therein, printing an edible media to form a portion of the 3D shell corresponding to the model for introduction of the medicament, and then printing the edible media to form the remainder of the 3D shell to completely enclose the medicament within the edible media.

20 Claims, 5 Drawing Sheets

(56) References Cited

U.S. PATENT DOCUMENTS

| | | | |
|---|---|---|---|
| 6,358,546 B1 | 3/2002 | Bebiak et al. | |
| 8,465,777 B2 | 6/2013 | Wang et al. | |
| 8,501,218 B2 | 8/2013 | Hurwitz | |
| 2002/0081356 A1* | 6/2002 | Bebiak | A01K 5/02 426/232 |
| 2003/0017234 A1* | 1/2003 | Hentzel | B65D 5/503 426/106 |
| 2004/0166140 A1* | 8/2004 | Santini, Jr. | A61K 9/0009 424/424 |
| 2005/0255148 A1* | 11/2005 | Puma | A01K 13/003 424/442 |
| 2006/0246116 A1 | 11/2006 | Putz | |
| 2008/0268105 A1* | 10/2008 | Seitz | A23G 3/007 426/93 |
| 2010/0055257 A1* | 3/2010 | Hervig | A23G 3/0074 426/103 |
| 2011/0091522 A1* | 4/2011 | Murwitz | A61K 9/009 424/440 |
| 2011/0244010 A1 | 10/2011 | Doshi | |
| 2011/0280996 A1* | 11/2011 | Gustav | A23G 1/0069 426/103 |
| 2012/0251689 A1* | 10/2012 | Batchelder | A23G 1/0056 426/383 |
| 2012/0315333 A1* | 12/2012 | Zhou | A61K 9/2095 424/484 |
| 2012/0321703 A1* | 12/2012 | Kouri | A61K 9/4808 424/451 |
| 2013/0034633 A1* | 2/2013 | von Hasseln | B29C 67/0081 426/104 |
| 2013/0193621 A1* | 8/2013 | Daya | A61K 9/70 264/401 |
| 2014/0099351 A1* | 4/2014 | Adams | A61K 31/485 424/423 |
| 2014/0120229 A1* | 5/2014 | Mantell | B29C 67/0059 426/515 |
| 2014/0134320 A1 | 5/2014 | Chang et al. | |
| 2014/0154378 A1* | 6/2014 | von Hasseln | B29C 67/0081 426/274 |
| 2014/0234523 A1* | 8/2014 | Gustav | A23G 1/0073 426/631 |
| 2016/0088870 A1* | 3/2016 | Langeland | A23P 20/20 425/375 |

\* cited by examiner

3D PRINTING OF DIGESTIBLE SHELLS FOR MEDICAMENTS

TECHNICAL FIELD

The present disclosure relates to medicaments for consumption by humans and animals. In particular, the disclosure relates to the introduction of medicaments into an ingestible media.

BACKGROUND

Getting pets to take medicaments in pill or liquid form is difficult and frustrating. A limited number of pet medications are available in flavored chewable formats. However, most pet medicaments are not provided in this manner due to cost and shelf-life concerns. Thus, the pet owner or veterinarian is left with the uncomfortable task of cajoling or forcing an animal to ingest an undesirable medication. One traditional technique is to hold the pet's mouth open and introduce the medicament into the back of the throat of the animal. Of course, this is uncomfortable and distressing to the pet and not always successful.

Another approach is to embed a pill medicament in some food item that is desirable to the pet, such as butter, cheese, a hot dog, or commercially available pet treats such as Greenies® brand Pill Pockets®. While this approach is less invasive, it can be equally frustrating as the intelligent pet manages to enjoy the tasty food while somehow spitting out the medicament. Moreover, this approach is not well-suited to liquid medicaments.

The same issues arise with children, particularly with children that are too young to be "bribed" to swallow the medicine. Consequently, there is a need for a way to provide a medicament in a format that is easily and willingly ingested by pet or person. It is further desirable that a process for providing the medicament in this format be readily tailored to the form of the medication as well as the tastes of the recipient.

SUMMARY OF THE DISCLOSURE

A method is provided for producing edible medications based on three-dimensional printing of an edible media to form a shell for receiving a medicament. The method includes providing a three-dimensional (3D) model of the edible medication including an internal cavity sized and shaped for receipt of a medicament therein and then providing that model to a 3D printing machine. An edible media is fed to the 3D printing machine for printing a first portion of the 3D model. In one aspect, the first portion is configured to provide access to at least a portion of the cavity for introduction of the medicament. After the medicament is introduced into the partially formed cavity, the remaining portion of the 3D model is printed with the edible media to completely enclose the cavity and the medicament within the cavity.

In one aspect, the medicament may be a solid medicament, in which case the 3D model is printed leaving a bottom half of the cavity exposed for placement of the solid medicament. In a further aspect, the medicament may be a liquid medicament, in which case the 3D model is printed so that substantially the entire cavity is formed, leaving an opening at the top of the cavity for injection of the liquid medicament. The medicament may be introduced into the partially formed edible shell robotically or manually. In another aspect, the 3D model may include a plurality of edible medications formed in an array and configured for easy removal of the edible shells from the array.

DETAILED DESCRIPTION

For a general understanding of the present embodiments, reference is made to the drawings. In the drawings, like reference numerals have been used throughout to designate like elements. As used herein, the terms "3D printing" or a "3D printer" refer to processes and machines capable of forming three-dimensional shapes from a model by the sequential application of successive layers of a media. The 3D printing process is performed under computer control based on a model of the desired 3D shape stored in a memory. As used herein, the 3D printer includes a computer controller with a memory, and components for applying jettable media in thin layer under computer control. As used herein, a "jettable media" can be a settable composition that can be provided in an initial form that has a viscosity sufficiently low to be readily ejected from jets mounted on a movable carriage in the 3D printing machine or a solid media that changes to a low viscosity when heated so it can be ejected from jets then harden as it cools.

One example of a suitable 3D printer is the "CubeX™" 3D printer sold by 3D Systems, Inc. The CubeX™ 3D printer is configured to create 3D models from PLA or ABS plastic in layer thicknesses of 0.1-0.5 mm. The plastic material is heated within reservoirs in the printer and heated to achieve a viscosity that allows the material to be fed under pressure to one or more jets and discharged from the jets in a controlled pattern on a printing surface to form a discrete thin layer of material. The carriage supporting the jets is raised at each printing step to apply a new layer onto an existing layer that has at least partially cured. It is understood that certain modifications to the 3D printer may be necessary to accommodate the use of edible material as the jettable media. At a minimum, the working components will be cleanable and sterilizable to meet food handling regulations. Modifications to the heating protocol, reservoir, flow to the jets, and the jets themselves may also be warranted to handle the food grade media.

The embodiments disclosed herein relate to the preparation of medicaments for ingestion by an animal, and to a system and method for use by a veterinarian in dispensing medicaments to be administered by veterinary personnel or the pet owner. However, it is understood that the systems and methods disclosed herein may find application in other arenas, such as in the preparation of medicaments for human consumption and use by a pediatrician or pharmacist.

Figure 1:
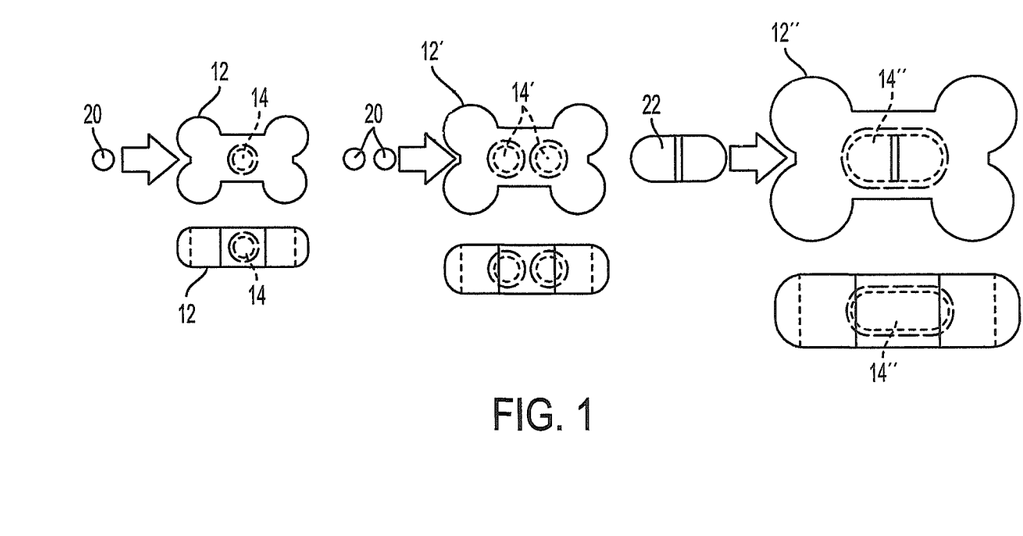
FIG. 1 is a top view of medicaments contained within an edible shell for ingestion by an animal.
Figure 2:
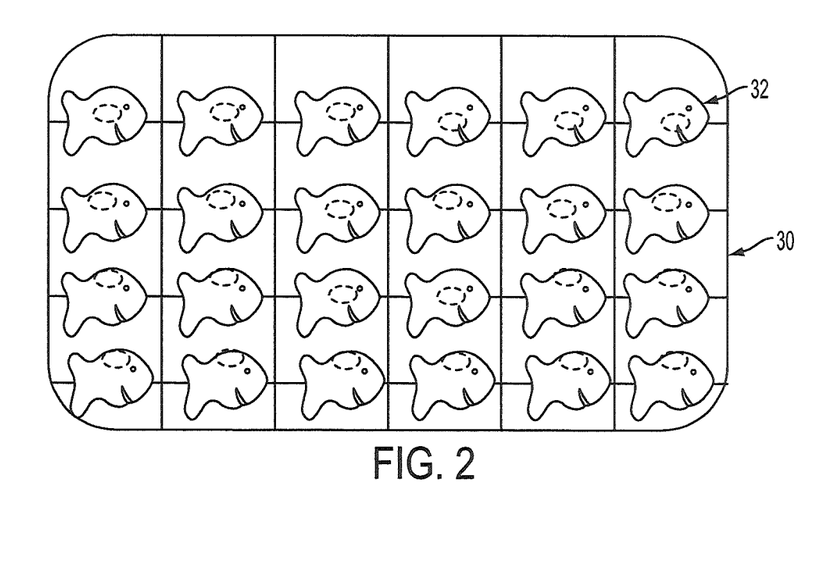
FIG. 2 is a plan view of an array of edible shells having a different configuration than the shells shown in FIG. 1.

The present disclosure provides a system and method for "building" a flavored shell around a medicament, whether in pill or liquid form, using a 3D printer and 3D printing process. In particular, a model corresponding to a particular edible shell configuration is generated according to the nature, size and shape of the medicament and other parameters. The additional parameters may include positioning of the medicament within the shell, the exterior configuration of the shell, the fluid properties of the media, etc. By way of example, different configurations of medicaments and edible shells are shown in FIG. 1. In one example, the edible shell 12 is produced to define an interior cavity 14 that is sized to receive a generally spherical medicament 20. The shell 12' is provided with two interior cavities 14' to receive two of the spherical medicaments 20. An oblong medicament 22 is received within an appropriately configure cavity 14" in the edible shell 12". In the illustrated examples, the shells 12, 12', 12" have the shape of a dog bone. Other shell shapes are possible, such as the goldfish shape of the shells 32 in the array 30 shown in FIG. 2. Moreover, other medicament shapes are possible, such as a disc shape, although most pill-type medication is provided in one of these three shapes. The medicament may be provided in other sizes as well, which require adjustment of the dimensions of the interior cavities.

Figure 3:
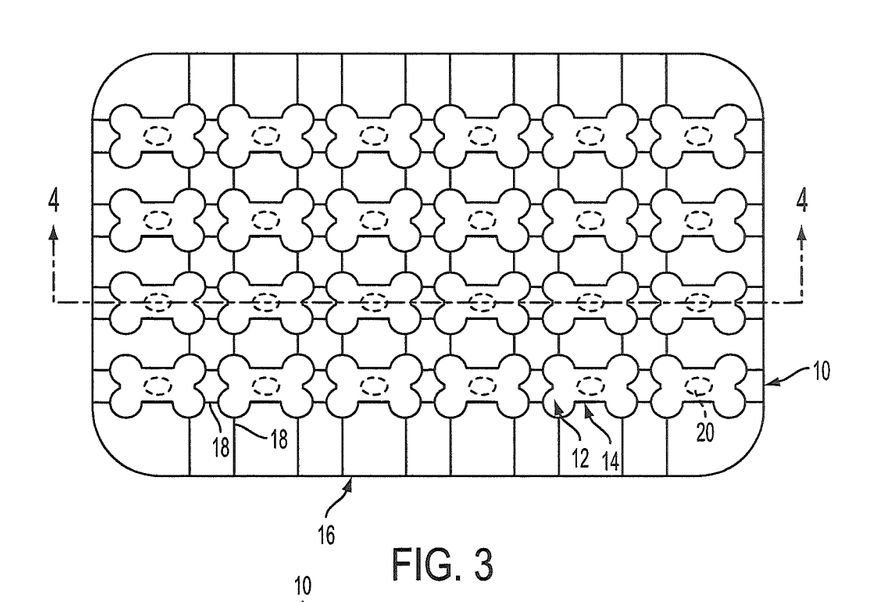
FIG. 3 is a plan view of an array of edible shells of the configuration shown in FIG. 1.
Figure 4:
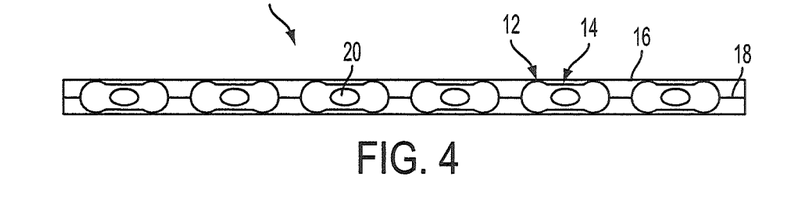
FIG. 4 is a side view of the array of edible shells shown in FIG. 4.

The 3D printer is configured to produce an array of the edible shells, such as the array 10 shown in FIGS. 3-4. The array 10 includes a plurality of shells 12 in a support structure including an outer frame 16 and supporting spars 18. The spars 18 are integrally printed with the shells but have a reduced cross-section so that the shells 12 can be readily severed from the spars 18. The spars 18 are arranged to adequately support the plurality of shells in the array for removal from the 3D printing machine and to maintain the integrity of the array as it is being formed layer-by-layer by the 3D printing machine. It is contemplated that the operator may cut the shells from the spars using a knife. Alternatively, the shells may be pressed from the array so that the shells mechanically separate from the spars without the use of a knife.

As is known, a 3D model is derived to control the operation of the 3D printing machine. The control software reads the model and directs the movement and operation of the jets accordingly layer by layer. In accordance with the present disclosure, a data base of 3D models may be accessed by the 3d printing software or a data base of design parameters may be accessed by software that then creates the 3D model. In the former case, the data base would include 3D models corresponding to particular medicament configurations and particular edible shell configurations. For example, the three configurations shown in FIG. 1 could be standard 3D models retained in the data base. In the later alternative, the model generation software utilizes information regarding the shape and dimensions of the medicament and the shape and dimensions of the edible shell to generate a 3D model of the shell, including the cavity configured to hold the medicament. The user, such as the veterinarian, supplies the requisite information to the 3D modeling software, which generates the model and conveys the model to the 3D printing software to control the operation of the 3D printing machine. It can be appreciated that the model produced by the modeling software can include the support structure 16, 18 according to a predetermined protocol to produce an array of shells, such as the array 10 shown in FIGS. 2-3.

It is further contemplated that a more sophisticated 3D modeling software may draw on a data base of medications which includes the volumetric properties of the medicaments. In this case, the user or veterinarian need only identify the medication, rather than provide the dimensions of the medicament. A data base may also be maintained for animal species to determine the appropriate configurations and dimensions for the edible shell. For instance, an edible shell intended for a Chihuahua is necessarily smaller than a shell intended to be consumed by a horse. The 3D modeling software may also access a personalization data base in which pet owner or veterinarian preferences can be stored, such as shell shapes or edible composition (i.e., flavoring, texture, etc.).

Figure 5:
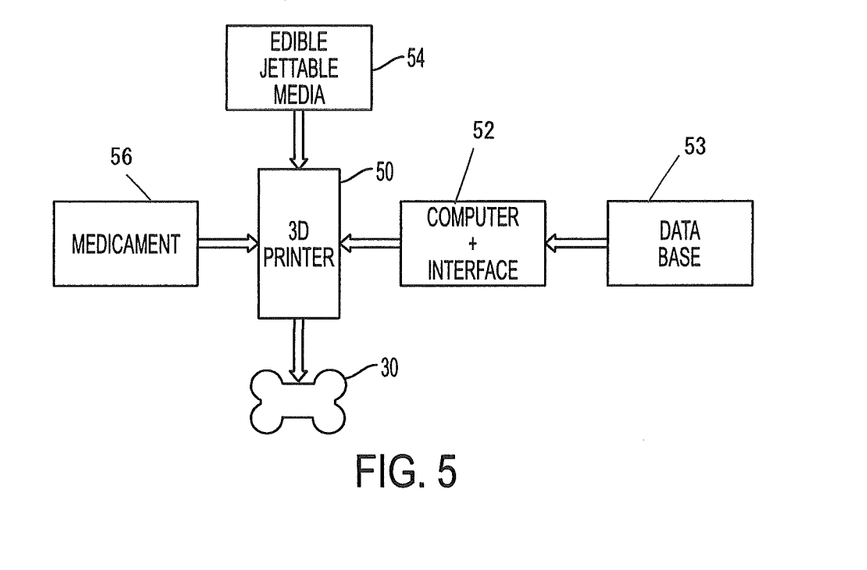
FIG. 5 is a block diagram showing components in the production of the edible shells shown in the prior figures.

A system for producing an edible 3D printed medication is depicted in FIG. 5. The heart of the system is the 3D printing machine 50 that is adapted to produce 3D products from an edible jettable media. The media is contained in a reservoir 54 that may be separate from or part of the printing machine 50. In one embodiment, the reservoir 54 is configured to contain a plurality of different edible jettable media, with a fluid transfer mechanism configured to convey a selected one of the media to the jets of the 3D printing machine 50. For instance, the jettable media can be a form of gelatin that hardens or sets with or without the application of heat. The plurality of media contained within the reservoir 54 may be the same gelatin composition with different flavoring, or may be different types of gelatin. It is contemplated that the array of edible media can encompass a wide range of media that are capable of use in a 3D printing procedure.

The 3D printing machine 50 may incorporate its own internal processor operable to execute software commands for controlling the components of the 3D printing machine, as is known in the art. In the system shown in FIG. 5, the printing machine may communicate with a computer and interface 52 that allows the user, such as a veterinarian, to tailor the finished product produced by the printing machine. In one aspect, the computer 52 may communicate with a data base 53 stored in a memory that may be part of the computer and interface 52, may be contained with a separate storage device, or may be accessible in the "cloud" or offsite storage using cloud computing or internet access schemes. The computer may execute software that allows the user to select among information stored in the data base 53, such as types of medicaments, types of edible media, configurations of the final product, customer/client preferences and the like. The software may also provide an avenue for the user to directly generate the data required by the 3D printing machine 50 to produce the 3D product, by way of the computer and interface 52. For instance, the use may desire to encapsulate a medicament that is not available in the data base 53, in which case the software executed by the computer would allow the user to enter dimensional properties of the medicament.

The 3D printing machine 50 may also integrate with a source of the medicament 56. In one embodiment, the medicament is provided separately by the user, as described below. In another embodiment, the medicament is contained within a container 56 that is accessed by the 3D printing machine 50 for introduction into a cavity formed in the 3D printed media. In one example, a solid pill or tablet form medicament may be extracted by a robotic arm associated with the printing machine and placed within a newly formed cavity, as described herein. For a liquid medicament in container 56 the medicament may be introduced into the newly formed cavity by a robotic nozzle, or may be treated by the 3D printing machine as another jettable media in which case the medicament is jetted into the newly formed cavity. Alternatively, the medicament, whether solid or liquid, may be manually introduced into the cavity by a technician.

In the case of an array, such as the array 10 shown in FIG. 3, the medicament may be introduced into multiple cavities in multiple shells 12. It can be appreciated that the 3D printing machine may be controlled so that all of the shells 12 in the array include the same edible media and the same medicament. However, the printing machine may also be controlled to allow for variation among any and all of the shells 12 of the array 10, such as different edible media for the same medicament and even different outer configurations for the end products.

Figure 6:
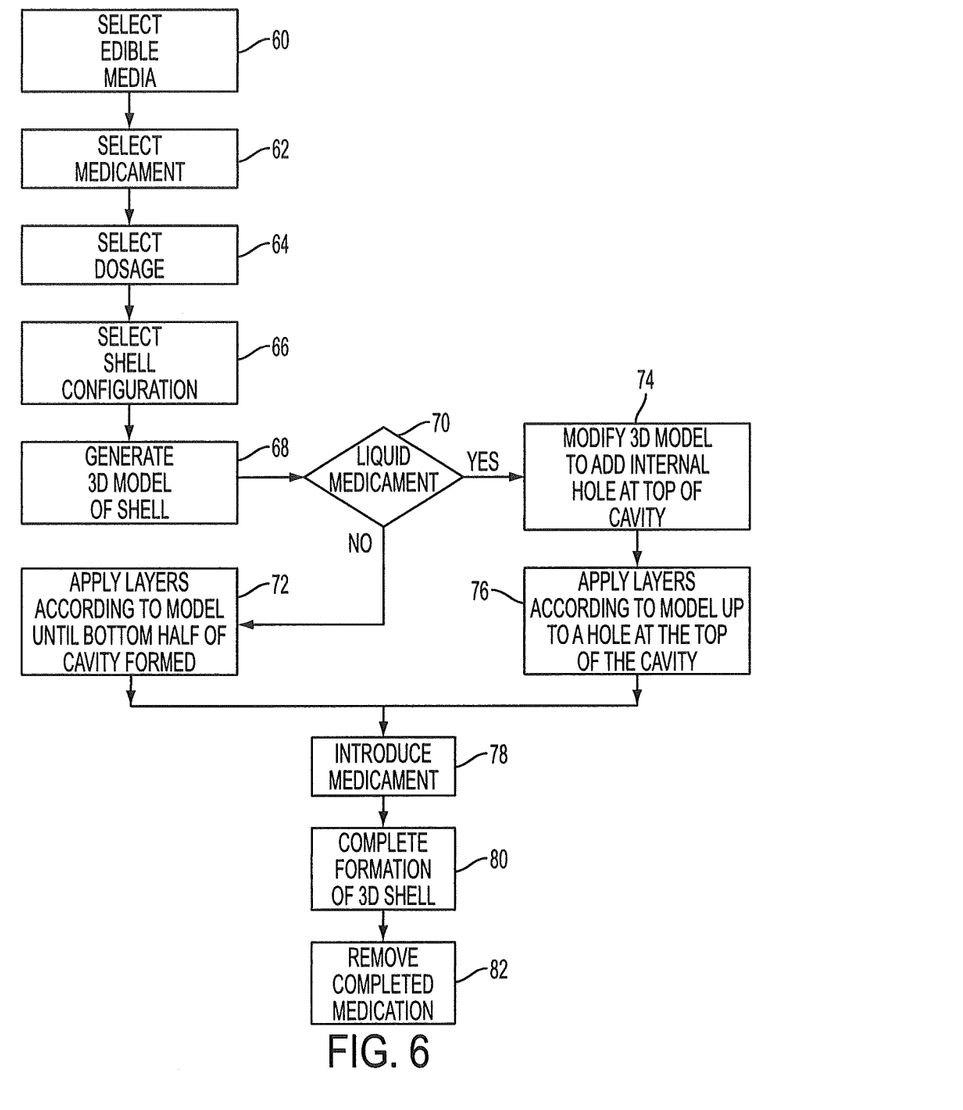
FIG. 6 is a flowchart of process steps in the production of the edible shells shown in the prior figures.

A flowchart of the process steps disclosed herein is shown in FIG. 6. In the first step 60, the user, such as the veterinarian, selects the edible jettable media. This selection can be made using the computer and interface 52 and can be obtained from the data base 53 or separately entered by the user, as discussed above. In the next step 62, the user selects the medicament, which again may be by way of the data base or by separate data entry. The dosage of the medicament may be selected in step 64, provided that the medicament is not already supplied in a fixe dosage. It is understood that the media and medicament selection process may be very limited, such as with only one available media and one available medicament, may be heavily data base oriented in which very specific media and medicaments are provided, and even specific limited combinations of media and medicament.

The software executed by the computer 52 may also permit user selection of the shell configuration in step 66. Thus, the user may again select from a data base of shape, such as the dog bone or goldfish configurations shown in FIGS. 2-3, as well as other standard shapes. Alternatively, the user may provide data for the configuration of the shell by entry through the computer interface.

The selection steps 60-66 all lead to step 68 in which the computer software generates a 3D model of the shell to be printed by the 3D printing machine 50. As is known, the 3D printing machine applies successive thin layers of the jettable media to form the 3D shape, complete with internal features such as the cavity 14. Each of the features and components selected in steps 60-66 imparts some definition to the 3D shape to be printed and the manner in which it is printed. For instance, the selection of media may determine the thickness of the layers, the duration of the jetting process or the delay before a subsequent layer is applied. The selection of medicament and dosage may determine the dimensions of the cavity 14 defined in the edible media. It is contemplated that the cavity dimensions are adapted for a close fit with the medicament in the case of a solid medicament or for a substantially identical volume for a liquid medicament dosage. The shell configuration selection obviously determines the outer dimensions and shape of the final product 10, 30 for instance. All of this data is used by the software to generate a 3D model in step 68 to be used by the 3D printing machine.

The final product is produced in the ensuing steps 72-80. In one aspect, the medication preparation process contemplates a final product with either a solid or a liquid medicament. The 3D printing process is modified according to the state of the medicament. Thus, in step 70 a determination is made as to whether the medicament is solid or liquid. In the case of a solid medicament, the control software directs the 3D printing machine to print the 3D shape, or apply the successive media layers, only until the bottom half of the cavity 14 is formed in step 72. At this point, the medicament is introduced in step 78 by placing the solid medicament obtained from the container 56 within the partially formed cavity. In one embodiment the medicament is placed robotically by a machine associated with the printing machine 50.

In another embodiment, the computer and/or printing machine may alert a technician to manually place the medicament in the cavity. Once the medicament has been placed, the 3D printing process continues to complete the formation of the shell around the medicament in step 80, leading to removal of the final product in step 82.

If the medicament is a liquid, the control passes from step 70 to step 74 in which the 3d model is modified to add an internal hole at the top of the cavity 14. This hole is sized for introduction of the liquid medicament, such as through a nozzle or syringe. Once the model is modified, the 3D printing machine applies the layers of the selected media in step 76 according to the revised model up to the printing of the hole. At that point, the entire cavity and surrounding media has been formed so that only a hole is visible that communicates with the interior of the cavity 14. At this point, the liquid medicament is introduced through the hole into the cavity in step 78. As with the solid medicament, the liquid medicament may be robotically or manually introduced as described above. Once the cavity 14 has been filled with the liquid medicament, the 3D printing machine is directed to complete the formation of the shell in step 80 in which the internal hole is covered with media so that the final product removed in step 82 is complete and fully contained.

It will be appreciated that variants of the above-disclosed and other features, and functions, or alternatives thereof, may be desirably combined into many other different systems or applications. Various presently unforeseen or unanticipated alternatives, modifications, variations, or improvements therein may be subsequently made by those skilled in the art, which are also intended to be encompassed by the following claims.

What is claimed is:

1. A method for producing edible medications comprising:
   providing a three-dimensional (3D) model of the edible medication including an internal cavity sized and shaped for receipt of a medicament therein;
   providing the 3D model to a 3D printing machine;
   feeding an edible media to the 3D printing machine;
   printing a first portion of the 3D model with a plurality of layers of the edible media forming at least a portion of the internal cavity, the at least a portion of the internal cavity being empty and without any medicament located in the at least a portion of the internal cavity, the first portion configured to provide access to the at least a portion of the internal cavity;
   after printing the first portion, introducing a medicament into the at least a portion of the internal cavity; and
   after introducing the medicament, printing a remaining portion of the 3D model with another plurality of layers of the edible media completely enclosing the internal cavity and the medicament within the internal cavity.

2. The method of claim 1, wherein the medicament is a solid medicament.

3. The method of claim 2, wherein providing the 3D model includes using physical 3D dimensions and configuration of the solid medicament to define a size and shape of the internal cavity.

4. The method of claim 3, wherein providing the 3D model includes defining the size and shape of the internal cavity to correspond to a size and shape of the solid medicament.

5. The method of claim 2, wherein:
   printing the first portion of the 3D model includes printing the first portion of the 3D model so that the at least a portion of the internal cavity corresponds to a lower half of the solid medicament; and introducing the medicament includes placing the solid medicament in the at least a portion of the internal cavity with an upper half of the solid medicament extending out of the at least portion of the internal cavity.

6. The method of claim 5, wherein the solid medicament is robotically placed in the at least a portion of the internal cavity.

7. The method of claim 5, wherein the solid medicament is manually placed in the at least a portion of the internal cavity.

8. The method of claim 1, wherein the medicament is a liquid medicament.

9. The method of claim 8, wherein providing the 3D model includes defining a volume of the internal cavity to receive the liquid medicament.

10. The method of claim 9, wherein the step of providing a 3D model includes defining a size and shape of the internal cavity to provide a volume that corresponds to a predetermined dosage of the liquid medicament to be introduced into the internal cavity.

11. The method of claim 8, wherein
printing the first portion of the 3D model includes printing the first portion of the 3D model so that the at least a portion of the internal cavity is enclosed by at least one layer having an opening to enable the liquid medicament to be introduced into the internal cavity through the opening; and
introducing the medicament includes injecting the liquid medicament through the opening into the internal cavity.

12. The method of claim 11, wherein the liquid medicament is injected until the liquid medicament fills the internal cavity.

13. The method of claim 11, wherein the liquid medicament is robotically injected through the opening into the internal cavity.

14. The method of claim 11, wherein the liquid medicament is manually injected through the opening into the internal cavity.

15. The method of claim 1, wherein providing the 3D model includes selecting an external shell configuration and providing a 3D model according to the selected shell configuration.

16. The method of claim 1, wherein feeding the edible media includes selecting an edible media from a plurality of edible media and then feeding the selected edible media to the 3D printing machine.

17. The method of claim 16, wherein providing the 3D model includes using data pertaining to physical characteristics of the selected edible media to generate the 3D model before providing the 3D model to the 3D printing machine.

18. The method of claim 1, wherein introducing the medicament includes selecting the medicament from a plurality of medicaments and then introducing the selected medicament.

19. The method of claim 18, wherein the providing the 3D model includes using data pertaining to physical characteristics of the selected medicament to generate the 3D model before providing the 3D model to the 3D printing machine.

20. The method of claim 1, wherein providing the 3D model includes providing a 3D model of a plurality of edible medications within an array configured for subsequent removal of the medications from the array.

* * * * *